Figure 1:
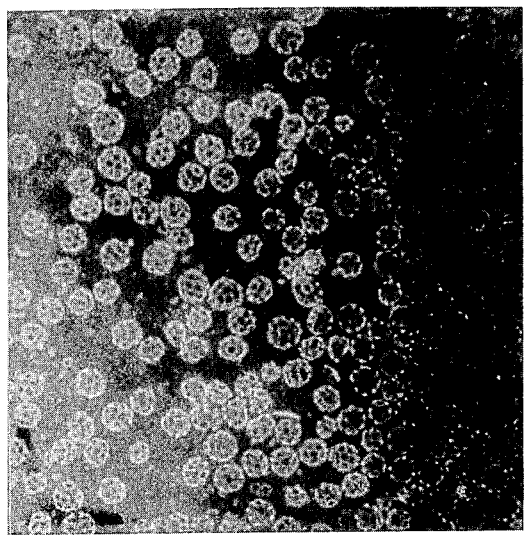

United States Patent [19]

De Vries et al.

[11] Patent Number: 4,900,549
[45] Date of Patent: Feb. 13, 1990

[54] PROCESS FOR PREPARING IMMUNOGENIC COMPLEXES AND PHARMACEUTICAL COMPOSITION CONTAINING THESE COMPLEXES

[75] Inventors: Petra De Vries, Almere; Antonius L. van Wezel, deceased, late of Bilthoven, by Cornelia M. van Wezel-Berendse, administratrix; Eduard C. Beuvery, Vianen, all of Netherlands

[73] Assignee: De Staat der Nederlanden Vertegenwoordigd door de Minister van Welzion, Volksgezondheid en Cultuur, Leidschendam, Netherlands

[21] Appl. No.: 3,070

[22] Filed: Jan. 14, 1987

[30] Foreign Application Priority Data

Jan. 14, 1986 [NL] Netherlands ............... 8600066

[51] Int. Cl.$^4$ ............... A61K 9/66; A61K 9/64; A61K 37/22; A61K 39/39
[52] U.S. Cl. ............... 424/88; 424/89; 424/92; 424/450; 424/420; 424/418; 424/491; 424/498; 424/499; 514/8; 514/21; 514/42; 514/885
[58] Field of Search ............... 424/88, 89, 90, 91, 424/92, 450, 420, 418, 491, 498, 499; 514/8, 21, 42, 885

[56] References Cited

U.S. PATENT DOCUMENTS

| | | | |
|---|---|---|---|
| 4,053,585 | 10/1977 | Allison et al. | 424/92 |
| 4,196,191 | 4/1980 | Almeida et al. | 424/89 |
| 4,201,767 | 5/1980 | Fullerton et al. | 424/89 |
| 4,354,977 | 10/1982 | Hoskinson et al. | 530/390 |
| 4,356,169 | 10/1982 | Simons et al. | 424/89 |
| 4,386,066 | 5/1983 | O'Rourke et al. | 424/92 |
| 4,438,052 | 3/1984 | Weder et al. | 424/88 |
| 4,439,199 | 3/1984 | Amkraut et al. | 424/88 |
| 4,578,269 | 3/1986 | Morein | 424/89 |
| 4,806,350 | 2/1989 | Gerber | 424/88 |

FOREIGN PATENT DOCUMENTS

| | | |
|---|---|---|
| 0047480 | 3/1982 | European Pat. Off. . |
| 0109942 | 5/1985 | European Pat. Off. . |
| 0142192 | 5/1985 | European Pat. Off. . |
| 0142193 | 5/1985 | European Pat. Off. . |
| 0180564 | 5/1986 | European Pat. Off. . |

OTHER PUBLICATIONS

Morein et al., J. Gen. Virol., 64,1557-69, 1983.
Skelly et al., Nature, 290, 51-5, 1981.
Nature, vol. 308, Mar. 29, 1984; pp. 457-460, Chesham, Bucks, GB: B. Morein et al.: "Iscom, a Novel Structure for Antigenic Presentation of Membrane Proteins from Enveloped Viruses", Entirely.
Bull. Off. Int. Epiz., 77, 1289-1295 (1972), K. Dalsgaard.
K. Dalsgaard—Archiv fur die Gesamte Virusforschung, 44, 243-254 (1974).
T. Patt & W. Winkler; Arzneimittelforschung, 10 (4), 273-275 (1960).
R. Vochten et al., J. Pharm. Belg., 42, 213-226 (1968).
Develop. Biol. Standard., 42, 65-69 (1978).
Anal. Biochem., 83, 346-356 (1977).
Blake & Gotschlich; J. Exp. Med., 159, 452-462 (1984).
Infect. Immuno., 40: 369-380 (1983).

*Primary Examiner*—Margaret Moskowitz
*Assistant Examiner*—Jeff Kushan
*Attorney, Agent, or Firm*—Brumbaugh, Graves, Donohue & Raymond

[57] ABSTRACT

The invention relates to a process for preparing immunogenic complexes in which an amphiphatic antigenic protein or peptide in dissolved or solubilized form is contacted with a solution containing a detergent, a sterol, and a glycoside comprising hydrophobic and hydrophilic regions, in at least the critical micelle forming concentration, the detergent is removed, and the immunogenic complex formed is purified. Optionally, the solution with which the antigenic protein or peptide is contacted also contains a phospholipid, preferably phosphatidylethanolamine. The preferred sterol is cholesterol, and preferred glycosides are saponins, especially Quil A.

The immunogenic complex is useful as a vaccine. Its immunogenic power is higher than that of corresponding micelles formed by aggregation of the antigens, and is also higher than that of the antigens incorporated in liposomes.

15 Claims, 5 Drawing Sheets

PROCESS FOR PREPARING IMMUNOGENIC COMPLEXES AND PHARMACEUTICAL COMPOSITION CONTAINING THESE COMPLEXES

The invention relates to a process for preparing immunogenic complexes, among which those of the type which has been called "iscom" by B. Morein et al. in Nature 308 (1984), pages 457-460 (see also EP-A 0 109 942).

According to B. Morein et al. the iscoms are obtained by mixing micro-organisms, animal cells, proteins or peptides with solubilizing agents in buffered solution and contacting this solution, optionally after removal of the solubilizing agents, with a glycoside solution containing one or more glycosides with hydrophobic and hydrophilic regions, in a concentration of at least the critical micellular concentration. In this way the so-called "iscom" protein complex is formed, which is then purified. This purification may be carried out by means of gradient centrifugation, dialysis, chromatography or by means of other metnhods. Quil A extracted from the bark of Quillaja saponaria Molina is preferably used as glycoside.

Iscoms have been shown by electron micrography to possess a specific structure. Iscoms are particles having an average diameter of about 35 mm. Each particle has a loose, translucent, cage-like structure with ring-like sub-units about 12 nm in diameter. In case of membrane proteins of para-influenza-3, measles and rabies virus the immunogenic activity of the iscoms was shown to be at least 10 times higher than that of micelles formed by aggregation of the membrane proteins.

In EP-A 0 109 942 it is emphasized that the iscoms are distinguished from liposomes not only by their structure and by the presence of glycosides, but also by the fact that the iscoms would not contain lipids. It was now found, however, that with purified antigenic proteins and Quil A iscoms cannot be obtained. Further investigation has shown that the known iscoms do contain lipids, viz. cholesterol, which substances, apparently, are liberated by the solubilizing agent from the microorganisms, among which gram-negative bacteria or enveloped viruses, together with the antigenic proteins.

It was found that the iscom structure described by Morein et al. can be obtained only, if together with a sterol, such as cholesterol, also a phospholipid, such as phosphatidylethanolamine is present. In case a phospholipid is absent, the products obtained do not have the cage-like structure with a mean diameter of about 35 nm characteristic for the iscoms, but the product is more or less two-dimensional aggregate of the iscom subunits with a diameter of about 12 nm. It was found that these structures also form immunogenic complexes with antigenic proteins or peptides, which complexes, in comparison with micelles formed by aggregation of antigenic proteins, show a considerably improved immunogenic activity.

The invention relates to a process for preparing immunogenic complexes, in which an amphipathic antigenic protein or peptide in dissolved or solubilized form is contacted with a solution containing a detergent, a sterol, and a glycoside having hydrophobic and hydrophilic regions, in at least the critical micelle forming concentration, removing the detergent and purifying the immunogenic complex formed.

In case it is contemplated to prepare immunogenic complexes having an iscom structure the solution with which the antigenic protein or peptide is contacted also contains a phospholipid.

Figure 2:
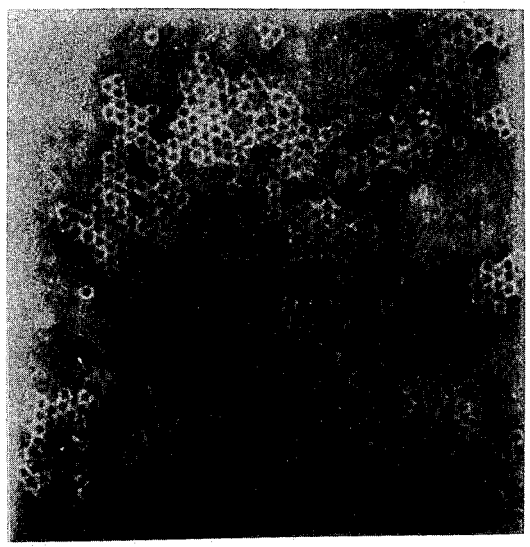
Figure 3A:
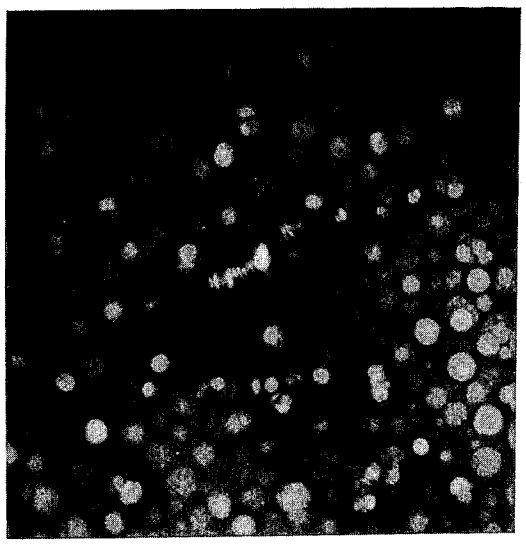
Figure 3B:
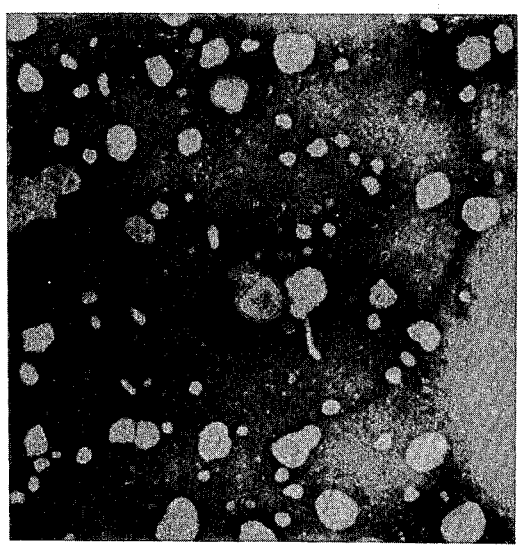

The use of glycoside, sterol, and phospholipid has been shown to be essential for the formation of iscoms, whereas the pure antigenic proteins or peptides do not play any role in this respect. Thus, it has been shown that, without antigen, iscoms are formed from glycoside, sterol and phospholipid. An electron micrograph of iscoms obtained from Quil A, cholesterol and phosphatidylethanolamine is depicted in FIG. 1 (magnification 116,000×). In case phospholipids are not used two-dimensional structures are formed. An example of such structures is depicted in FIG. 2. This figure is an electron micrograph (magnification 146,000×) of structures obtained from Quil A and cholesterol. In case sterol is omitted from the mixture liposome-like structures are obtained, the preparation of which does not belong to the invention. FIG. 3a is an electron micrograph of such structures obtained with Quil A and phosphatidylcholine (magnification 146,000×), and FIG. 3b is an electron micrograph of structures obtained from Quil A and phosphatidylethanolamine (magnification 89,000×).

The glycosides to be used in the process according to the invention are the saame as those mentioned in EP-A 0 109 942. Generally, the glycosides are glycosides showing amphipathic properties, and comprise hydrophobic and hydrophilic regions in the molecule. Preferably, saponins are used, especially the saponin extract from Quillaja saponaria Molina, in the first place DQ-extract prepared according to K. Dalsgaard: Saponin Adjuvants, Bull. Off. Int. Epiz. 77 7-8), 1289-1295 (1972) and Quil A, also prepared according to K. Dalsgaard: Saponin Adjuvants III, Archiv für die gesamte Virusforschung 44, 243-254 (1974). Other preferred saponins are aescine from Aesculus hippocastanum (T. Patt and W. Winkler: Das therapeutisch wirksame Prinzip der Rosskastanie (Aesculus hippocastanum), Arzneimittelforschung 10 (4), 273-275 (1960) and sapoalbin from Gypsophilia struthium (R. Vochten, P. Joos and R. Ruyssen: Physicochemical properties of sapoalbin and their relation to the foam stability, J. Pharm. Belg. 42, 213-226 (1968)). The use of Quil A is especially preferred.

In the process according to the invention the glycosides are used in at least the critical micelle forming concentration. In the case of Quil A this concentration is 0.03% by wt.

The sterols used in the process according to the invention are the known sterols of animal or vegetable origin, such as cholesterol, lanosterol, lumisterol, stigmasterol and sitosterol. Preferably, cholesterol is used as the sterol in the process according to the invention.

According to the invention, phospholipids which are necessary for the preparation of iscoms are phosphatidic acid and esters thereof, such as phosphatidylcholine and phosphatidylethanolamine. The best results have been obtained with phosphatidylethanolamine.

In case the antigenic protein or peptide is water-insoluble it has to be solubilized. This can be effected in a known way by means of a detergent, with urea or with guanidine.

The detergents to be used for the solubilization of the antigenic protein or peptide, and in the sterol, glycoside and optionally phospholipid containing solution, are the same as those mentioned in EP-A 0 109 942. Generally, a non-ionic, ionic of zwitter-ionic detergent or a cholic acid based detergent, such as sodium desoxycholate can be used for this purpose. Preferably, the detergent used is octylglucoside, but alkylphenylpolyoxyethylene ethers are also suitable, especially a polyethylene glycol p-iso-octylphenylether having 9 to 10 oxyethylene groups which, e.g. is commercialized under the trade name Triton X-100 ®.

The process according to the invention may be used for the preparation of immunogenic complexes, among which iscoms, from antigenic proteins or peptides which have to show amphipathic properties. These proteins or peptides may be membrane proteins or membrane peptides isolated from viruses, bacteria, mycoplasma's, parasites or animal cells. It is known that the serine and threonine radicals present in the hydrophobic region (the membrane domain) of some viral membrane proteins may be esterified. Nonmembrane proteins and non-membrane peptides without the desirable hydrophobic properties may be incorporated into the immunogenic complexes after coupling these with peptides consisting of hydrophobic amino acids, with fatty acid radicals, with alkyl radicals, and the like. The proteins or peptides may also be prepared synthetically or by means of recombinant DNA-techniques. Generally, ultracentrifugation or dialysis is not sufficient for the purification of an antigenic protein or peptide of natural origin. Preferably, the antigens are purified by means of chromatography, e.g. on a column of DEAE-Sephadex or by means of immuno affinity chromatography.

In the process according to the invention the dissolved or solubilized antigen is generally contacted with a solution containing the glycoside in at least the critical micelle forming concentration, a sterol, and optionally a phospholipid. After this the detergent is removed and the immunogenic complex formed is purified.

Known methods can be used for the removal of the detergent, such as dialysis, gradient centrifugation or chromatography. When gradient centrifugation or chromatographic methods, e.g. gel filtration, are used for the removal of the detergent the immunogenic complex is also extensively freed from other substances such as excess glycoside and sterol. Generally, a dialysis is not sufficient for the purification of the immunogenic complexes, although removal of the detergent by dialysis results in formation of the immunogenic complexes.

If desired, the solutions of the immunogenic complexes obtained may be lyophilized. The lyophilized preparations may then be reconstituted before use by addition of water.

Further, the invention relates to a pharmaceutical composition containing immunogenic complexes prepared by means of the present process. These preparations may be obtained by bringing the immunogenic complexes in a form suitable for parenteral administration. Generally, the pharmaceutical compositions contain the immunogenic complexes in an aqueous, physiologically acceptable medium, which, if desired, contains a buffer and/or a salt such as sodium chloride for adaptation of the osmotic pressure.

The pharmaceutical compositions according to the invention show a substantially stronger immunogenic effect than compositions in which the antigenic protein or peptide is present in the form of aggregates.

In the following examples the preparation of the immunogenic complexes is illustrated further.

Example I (Iscoms containing measles fusion protein)

Cultivation of measles virus and purification of the fusion protein

Measles virus (a plaque variant of the Edmonston strain) was cultivated in the usual way (Develop. Biol. Standard. 42, 65–69, (1978)). The various suspension was filtered and concentrated via an Amicon hollow fiber cartridge (H10X100). The viral glycoproteins (haemagglutinin and fusion protein) were dissolved in 10 mM Tris-HCl (pH 7.8), 150 mM NaCl, 600 mM KCl, 0.1 mM $MgCl_2$, 2% (vol/vol) Triton X-100 ® and 1 mM phenylmethylsulfonylfluoride (J. Gen. Virol. 65, 355–366 (1984)). After solubilisation and ultracentrifugation (100,000×g, 60 min.) the fusion protein was removed from the supernatant by immuno-affinity chromatography. To this end monoclonal antibodies against the fusion protein were covalently bonded to Sepharose 4B (Pharmacia). The fusion protein was eluted with 5M $NH_4SCN$ in 20 mM Tris-HCl pH 7.8, 1 mM EDTA and 2.0% (wt./vol.) octylglucoside. $NH_4SCN$ was removed from the eluate by dialysis against 10 mM Tris-HCl (pH 7.8) and 150 mM NaCl. The eluate was analyzed with SDS-PAGE and the protein content in the eluate was estimated (Anal. Biochem. 83, 346–356 (1977)).

Incorporation of the fusion protein into iscoms

Figure 4:
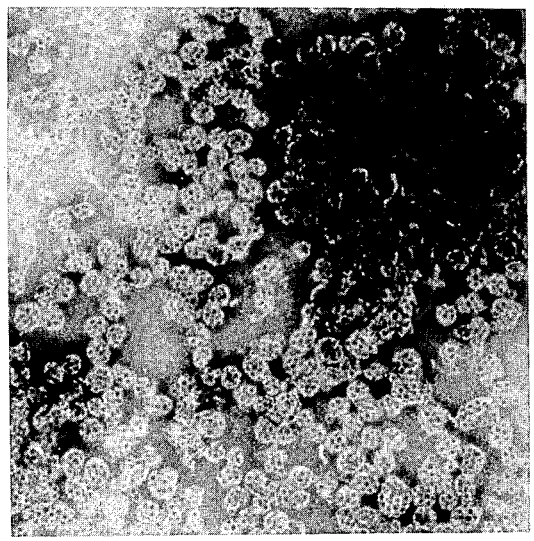

Fusion protein (60 µg) in 180 µl Tris-HCl (pH 7.8), 150 mM NaCl and 2% octylglucoside were mixed with 350 µg phosphatidylethanolamine and 350 µg cholesterol in 700 µl 2% octylglucoside. After one hour incubation at room temperature 1.7 mg Quil A as a 10% (wt./vol.) stock solution was added. The octylglucoside was removed by dialysis against 10 mM Tris-HCl (pH 7.8) and 150 mM NaCl during 16 hours at 4° C. The iscoms containing the fusion protein were purified by means of an ultracentrifugation in a continuous sucrose gradient (10–60% wt./vol.) (286,000×g, 4 h or 64,000×g, 18 h). The gradient was collected in 22 fractions (fraction 1, bottom fraction (highest density); fraction 22, top fraction (lowest density)). The fractions were analyzed with SDS-PAGE. The fractions containing the fusion protein were examined with the electron microscope. An electron micrograph of the iscoms containing the fusion protein is depicted in FIG. 4 (magnification 95,000×).

Figure 5:
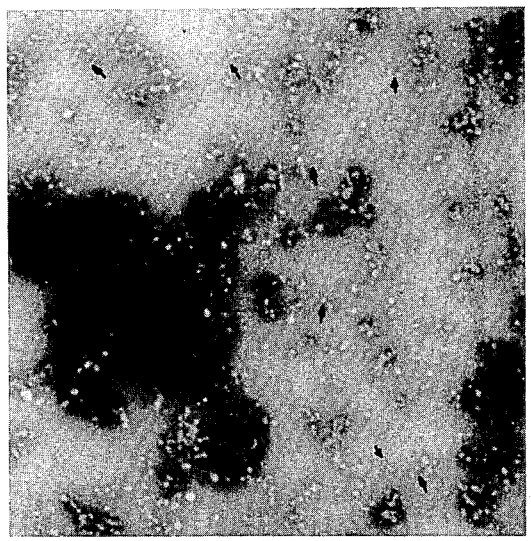

When the same process was carried out without addition of phosphatidylethanolamine and cholesterol iscoms were not formed. The result is shown in FIG. 5 (magnification 95,000×).

Example II (iscoms containing gonococcal porine proteins)

Cultivation of gonococcal strains

Gonococcal strains B2 (serotype 1) and C3 (serotype 5) were cultivated in the usual way. The cultures were inactivated by heating at 56° C. during 30 minutes. After centrifugation the bacteria were lyophilized. The cell-free culture liquid of the C3-strain was used for the preparation of the outer membrane complex (OMC), and the porine proteins (PI) were prepared from the lyophilized bacteria.

Preparation of outer membrane complexes (OMC)

The cell-free culture liquid was concentrated 80× by means of an Amicon hollow fibre cartridge (H10P10).

The concentrate was centrifugated (10,000×g, 20 minutes) so as to remove any residual bacteria. The OMC was centrifuged off (2 h at 100,000×g), suspended in 60 mM Tris-HCl (pH 7.2) and 300 mM NaCl, and again centrifugated (2 h at 100,000×g) and finally suspended in distilled water to obtain a protein concentration of 2 mg/ml.

Purification of PI

The isolation procedure was based on the procedure used by Blake and Gotschlich for the isolation of protein II (J. Exp. Med. 159, 452–462 (1984)). Lyophilized gonococcae were extracted with 2.5 g 3-(N-tetradecyl-N,N-dimethyl-ammonium)-1-propane sulfonate (Z3-14) in 0.5M $CaCl_2$ at pH 4.0. After 1 hour intact cells and fragments were removed by centrifugation (20 minutes, 20,000×g). Ethanol was added to the supernatant to obtain a concentration of 20%. After 30 minutes the precipitated material was removed by centrifugation (20 minutes, 10,000×g). The supernatant was concentrated by ultrafiltration (Amicon hollow fibre cartridge H10X50); 50 mM Tris-HCl, 10 mM EDTA, 0.05% (wt./vol.) Z3-14, pH 8.0 (buffer A) were added and the volume was reduced by 50%; this procedure was repeated five times so as to remove completely the calciumchloride and the ethanol. Then the protein solution was brought upon a column of DEAE-Sepharose equilibrated with buffer A. The proteins were eluted with a linear gradient of 0.0 to 0.6M NaCl in buffer A. The fractions were analyzed with SDS-PAGE and the PI containing fractions were combined. The partially purified PI was brought upon a Sephacryl S-300 column previously equilibrated with 50 mM Tris-HCl, 200 mM NaCl, 10 mM EDTA, 0.05% (wt./vol.) Z3-14, pH 7.2. The PI containing fractions were combined. The product obtained was designated as purified PI. The protein from the C3 strain as used in this example was analyzed for the presence of cholesterol and phospholipids. For the latter analysis an inorganic phosphate determination was used. The protein was free of cholesterol and contained 1.5 mole of phosphate per mole of protein. Most probably, the phosphate derives from a lipopolysaccharide impurity.

Preparation of immunogenic complexes with PI

Purified PI of both of the strains was precipitated with ethanol, centrifuged and dissolved in 10 mM Tris-HCl (pH 7.8), 150 mM NaCl and 2% octylglucoside. These solutions were mixed with phosphatidylethanolamine, cholesterol and Quil A (see table A). The removal of the octylglucoside and the purification of the immunogenic complexes was carried out in accordance with example I. Further, a gel filtration step via Superose 6 (Pharmacia) was used instead of the ultracentrifugation step. Iscoms were eluted in the void volume of the column. Both of the purification step (dialysis and ultracentrifugation or column chromatography) could be carried out on the column by successively charging the column with 0.2% Quil A solution (about 2% of the column volume) and a mixture consisting of protein, detergent, phospholipid, cholesterol and Quil A. Also in this case iscoms were eluted in the void volume of the column.

The results described in the following part of this example relate to complexes obtained in accordance with the procedure described in Example I.

Immunisation of mice

Groups of 8 mice were injected intraperitoneally with PIC3 containing complexes. The dosage was 2.5 µg protein. Serum samples were collected after 4 weeks.

ELISA procedure

Antibody levels in the pooled serum samples were determined by coating microtiter plates with OMC, diluted with 0.15M NaCl. The subsequent steps were carried out as described in Infect. Immun. 40, 369–380 (1983)).

Analysis and immunogenic power of the complexes

The gradient fractions of the mixtures mentioned in table A were analyzed with SDS-PAGE. The result of the analysis of fractions 1–4 is mentioned in table B. The table shows that the addition of phosphatidylethanolamine and cholesterol, or of cholesterol only, influences the sedimentation behaviour of both of the PI's. The PI's in combination with phosphatidylethanolamine and cholesterol (mixtures 1 and 3) are found in the same fractions as the known iscoms. Mixture 4, in which cholesterol but no phosphatidylethanolamine has been incorporated, also gives complexes having a similar sedimentation behaviour. In contrast with this, the protein of mixture 2 in which neither cholesterol nor phosphatidylethanolamine has been incorporated, is found in totally different fractions (15–17).

Figure 6:
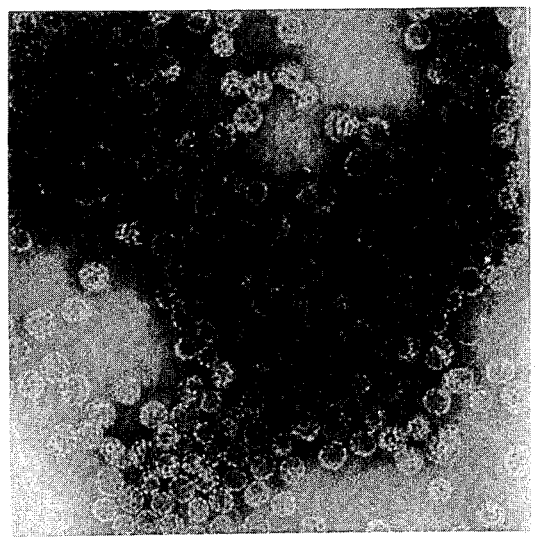
Figure 7:
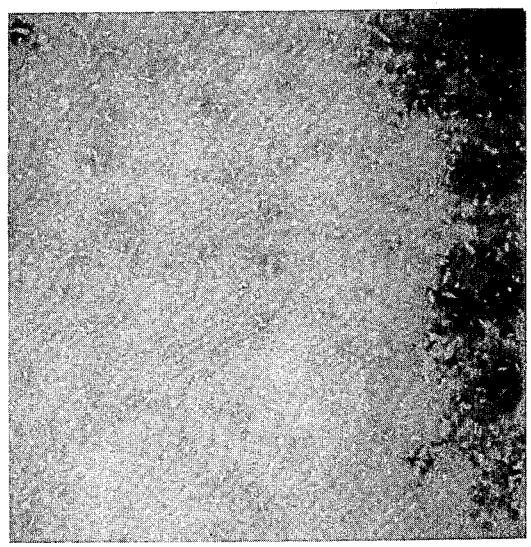
Figure 8:
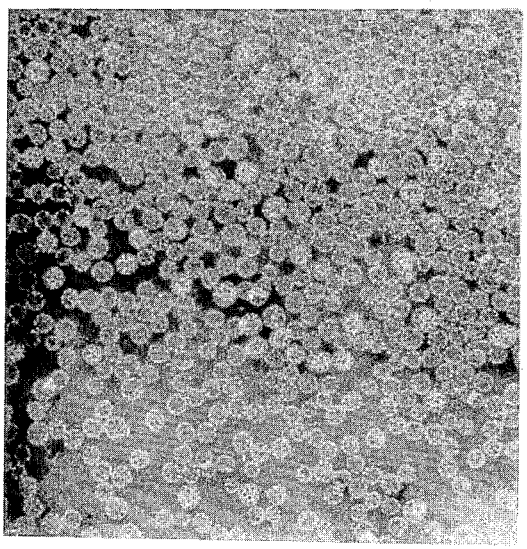
Figure 9:
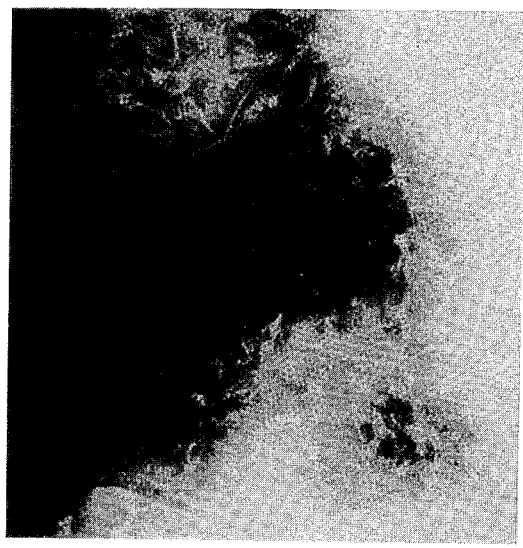

Per gradient, the fractions mentioned in table B were combined and, after dialysis, analyzed with the electron microscope. An electron micrograph of PIB2 containing iscoms (mixture 1) is shown in FIG. 6 (magnification 95,000×). When, however, the mixture was prepared without addition of phosphatidylethanolamine and cholesterol (mixture 2) iscoms were not obtained (see FIG. 7, magnification 95,000×). Photographs of the complexes obtained with mixtures 3 and 4 are depicted in FIG. 8 and FIG. 9, respectively (magnification 76,000×).

The iscoms prepared from mixture 6 had a strong tendency towards aggregation.

The cholesterol, Quil A and protein contents of the iscoms prepared from mixtures 1, 3, 5 and 6 were determined. The results are shown in Table C. The table shows that the three components were clearly detectable in the iscoms.

Antibody determination has shown that PIC3 in the iscoms and in the two-dimensional structures according to the invention is immunogenic. The immunogenic power of the protein in the iscoms and in the complex having the two-dimensional structure was higher than that of the protein incorporated in liposomes.

TABLE A

Composition of mixtures from which PIB2 and PIC3 containing complexes were prepared.

| protein type | mixture | composition of mixture before dialysis and ultracentrifugation* | | | |
| --- | --- | --- | --- | --- | --- |
| | | protein | phosphatidyl-ethanolamine | cholesterol | Quil A |
| PIB2 | 1 | 480 | 2,400 | 2,400 | 12,000 |
| PIB2 | 2 | 480 | — | — | 12,000 |
| PIC3 | 3 | 360 | 1,800 | 1,800 | 9,000 |
| PIC3 | 4 | 360 | — | 3,600 | 9,000 |
| PIC3 | 5 | 360 | 900 | 900 | 4,500 |

TABLE A-continued

Composition of mixtures from which PIB2 and PIC3 containing complexes were prepared.

| protein type | mixture | composition of mixture before dialysis and ultracentrifugation* | | | |
|---|---|---|---|---|---|
| | | protein | phosphatidyl-ethanolamine | cholesterol | Quil A |
| PIC3 | 6 | 360 | 450 | 450 | 2,250 |

*composition in /μg/ml

TABLE B

SDS-PAGE analysis of the gradient fractions after ultracentrifugation

| protein type | mixture | fractions shown to contain PI |
|---|---|---|
| PIB2 | 1 | 7-8-9 |
| PIB2 | 2 | 15-16-17 |
| PIC3 | 3 | 8-9 |
| PIC3 | 4 | 6-7-8 |

TABLE C

Composition of iscoms containing two different gonococcal porine proteins (PIB2 and PIC3). The PIC3 containing iscoms were prepared with varying protein/lipid ratios.

| protein type | mixture | Chol. (μg/ml) | QA (μg/ml) | Chol. QA | Protein (μg/ml) | QA: Protein |
|---|---|---|---|---|---|---|
| PIB2 (1:10)* | 1 | 163 | 100 | 1.6 | 85 | 1.2 |
| PIC3 (1:10) | 3 | 122 | 95 | 1.3 | 65 | 1.5 |
| PIC3 (1:5) | 5 | 64 | 74 | 0.9 | 55 | 1.3 |
| PIC3 (1:2.5) | 6 | 30.5 | 58 | 0.5 | 45 | 1.3 |

*protein/lipid ratio
Chol. = cholesterol
QA = Quil A

We claim:

1. A method for preparing immunogenic complexes in the form of particles having an average diameter of about 35 nm and a three-dimensional cage structure comprising (a) mixing an immunogenically effective amount of an amphipathic antigenic protein or peptide with a solution comprising a detergent, a glycoside, and a lipid component consisting essentially of a sterol and a phospholipid whereby a protein complex is formed, said lipid component being present in an amount by weight at least 2.5 times greater than the amount of protein, said glycoside having both hydrophobic and hydrophilic regions and being present in at least the critical micelle forming concentration, and said glycoside and said lipid component being present in relative amounts effective to produce three dimensional cage particles of 35 nm diameter; and (b) removing the detergent from the resulting protein.

2. A method for preparing immunogenic complexes that are substantially two dimensional aggregates of iscom subunits with a diameter of about 12 nm comprising (a) mixing an immunogenically effective amount of an amphipathic antigenic protein or peptide with a solution comprising a detergent, a glycoside, and a lipid component consisting essentially of a sterol which is substantially free of phospholipid whereby a protein complex is formed, said glycoside having both hydrophobic and hydrophilic regions and being present in at least the critical micelle forming concentration, said glycoside, and said lipid component being present in amounts such that 12 nm diameter two dimensional structures are formed, and said lipid component being present in an amount by weight at least 2.5 times the amount of the protein; and (b) removing the detergent from the resulting protein complex.

3. The process of claim 1 or 2, in which the glycoside is a saponin.

4. The process of claim 3, in which the saponin is a saponin from *Quillaja saponaria* Molina, *Aesculus hippocastanum* or *Gypsophilia struthium*.

5. The process of claim 4, in which the saponin is DQ, Quil A, aescine of sapoalbin.

6. The process of claim 5, in which the saponin is Quil A.

7. The process of claim 1 or 2, in which the sterol is cholesterol.

8. The process of claim 1, in which the phospholipid is phosphatidylethanolamine.

9. The process of claim 1 or 2, in which the detergent used is a non-ionic, ionic or zwitter-ionic detergent or a cholic acid based detergent.

10. The process of claim 9, in which the detergent is octylglucoside.

11. The process of claim 9, in which the detergent is an alkylphenylpolyoxyethylene ether.

12. The process of claim 11, in which the detergent is Triton X-100 ®.

13. The process of claim 1 or 2, in which the removal of the detergent from the protein complex is carried out by centrifugation in a density gradient, by dialysis or by chromatography.

14. Pharmaceutical composition comprising an immunogenic complex obtained by means of the process of any one of claims 3-13.

15. A method according to claim 1 or 2, wherein the ratio by weight of glycoside to the lipid component is about 2.5:1.

* * * * *

UNITED STATES PATENT AND TRADEMARK OFFICE
CERTIFICATE OF CORRECTION

PATENT NO. : 4,900,549

DATED : February 13, 1990

INVENTOR(S) : Petra De Vries et al.

It is certified that error appears in the above-identified patent and that said Letters Patent is hereby corrected as shown below:

Col. 1, line 28, "35 mm" should read --35 nm--;
Col. 2, line 27, "saame" should read --same--;
Col. 2, line 34, "7-8)" should read --(7-8)--;
Col. 3, line 1, "of" should read --or--;
Col. 5, line 58, "step" should read --steps--;

Col. 8, delete claim 14.

Signed and Sealed this

Sixteenth Day of June, 1992

Attest:

DOUGLAS B. COMER

Attesting Officer

Acting Commissioner of Patents and Trademarks